(12) United States Patent
Henry et al.

(10) Patent No.: US 7,065,402 B2
(45) Date of Patent: Jun. 20, 2006

(54) DETECTION OF POST-SHOCK THERAPY SINUSAL TACHYCARDIA IN ACTIVE IMPLANTABLE DEFIBRILLATOR CARDIOVERTOR MEDICAL DEVICES

(75) Inventors: Christine Henry, Paris (FR); Daniel Kroiss, Saint Ismier (FR)

(73) Assignee: ELA Medical S.A., Montrouge (FR)

( * ) Notice: Subject to any disclaimer, the term of this patent is extended or adjusted under 35 U.S.C. 154(b) by 631 days.

(21) Appl. No.: 10/270,206

(22) Filed: Oct. 11, 2002

(65) Prior Publication Data

US 2003/0097154 A1 May 22, 2003

(30) Foreign Application Priority Data

Oct. 12, 2001 (FR) .................................. 01 13135

(51) Int. Cl.
*A61N 1/39* (2006.01)
(52) U.S. Cl. ......................................................... 607/6
(58) Field of Classification Search .................... 607/4, 607/5, 6, 14; 600/518
See application file for complete search history.

(56) References Cited

U.S. PATENT DOCUMENTS

| 5,191,884 | A | 3/1993 | Gilli et al. |
| 5,462,060 | A | 10/1995 | Jacobson et al. |
| 5,545,186 | A * | 8/1996 | Olson et al. .................. 607/14 |
| 5,868,793 | A | 2/1999 | Nitzsche et al. |
| 5,978,707 | A * | 11/1999 | Krig et al. ..................... 607/14 |
| 6,151,524 | A | 11/2000 | Krig et al. |
| 6,178,350 | B1 | 1/2001 | Olson et al. |
| 6,671,548 | B1 * | 12/2003 | Mouchawar et al. .......... 607/14 |

* cited by examiner

*Primary Examiner*—Jeffrey R. Jastrzab
*Assistant Examiner*—Fernando Aguel
(74) *Attorney, Agent, or Firm*—Orrick Herrington & Sutcliffe LLP

(57) ABSTRACT

An active implantable medical device of the defibrillation/cardioverter type able to detect a post-therapy sinusal tachycardia. This device includes circuits and logic able to detect ventricular and atrial activity; episodes of tachycardia and deliver a therapy for defibrillation and/or cardioversion, and/or antitachycardia stimulation. The detected tachycardia are classified, and there is selective control for the delivery of therapy according to the type of detected tachycardia classified. The device conducts further analysis of tachycardia after delivery of a shock therapy and is able to determine the presence of a post-therapy sinusal tachycardia, preferably by recognition of a stable ventricular rate, a 1:1 association of ventricular and atrial rates, a ventricular heart rate that is located in a range corresponding to a slow ventricular tachycardia. The device also is able to inhibit the delivery of a therapy in the presence of determined post-therapy sinusal tachycardia.

11 Claims, 2 Drawing Sheets

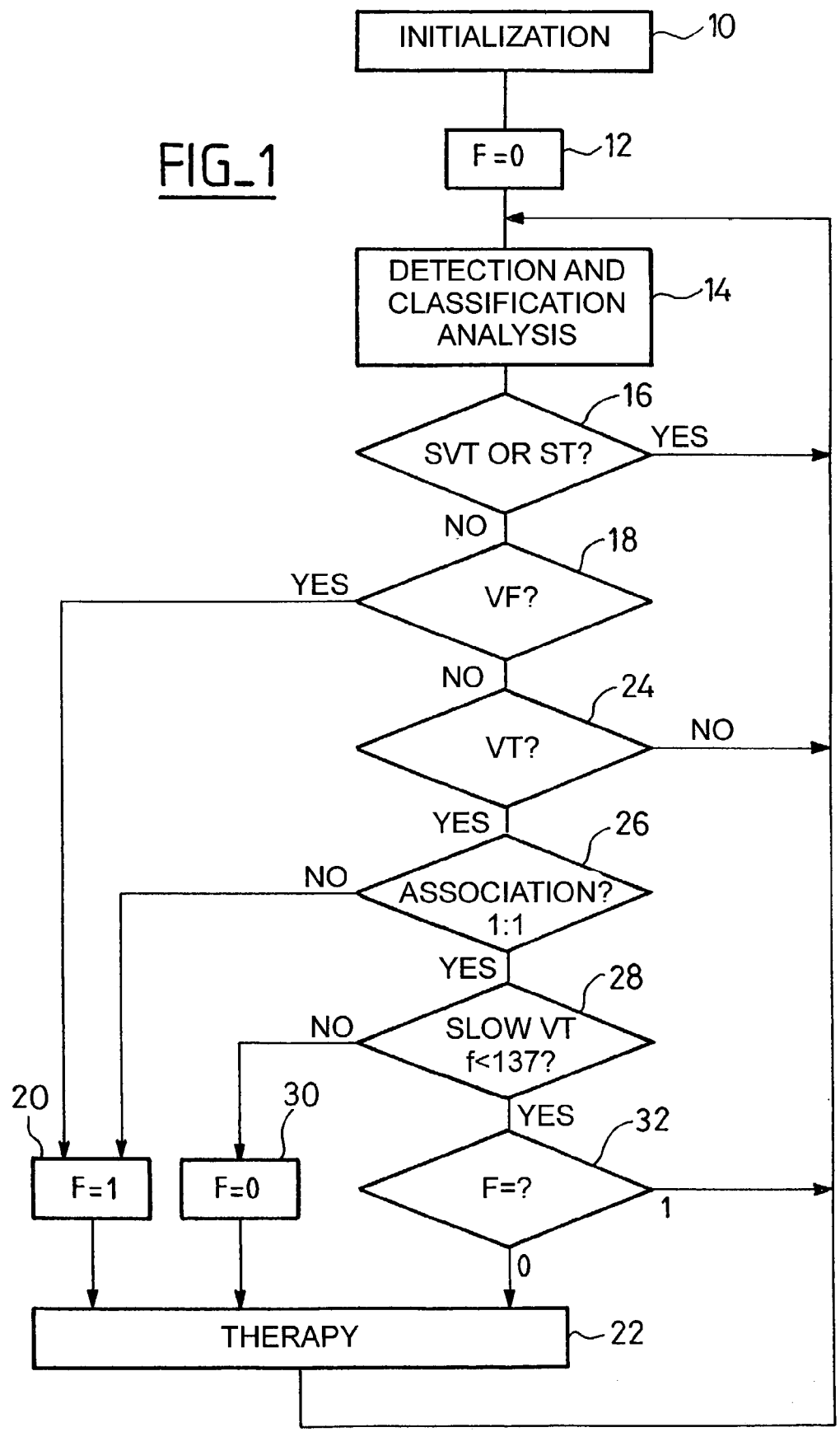
FIG_1

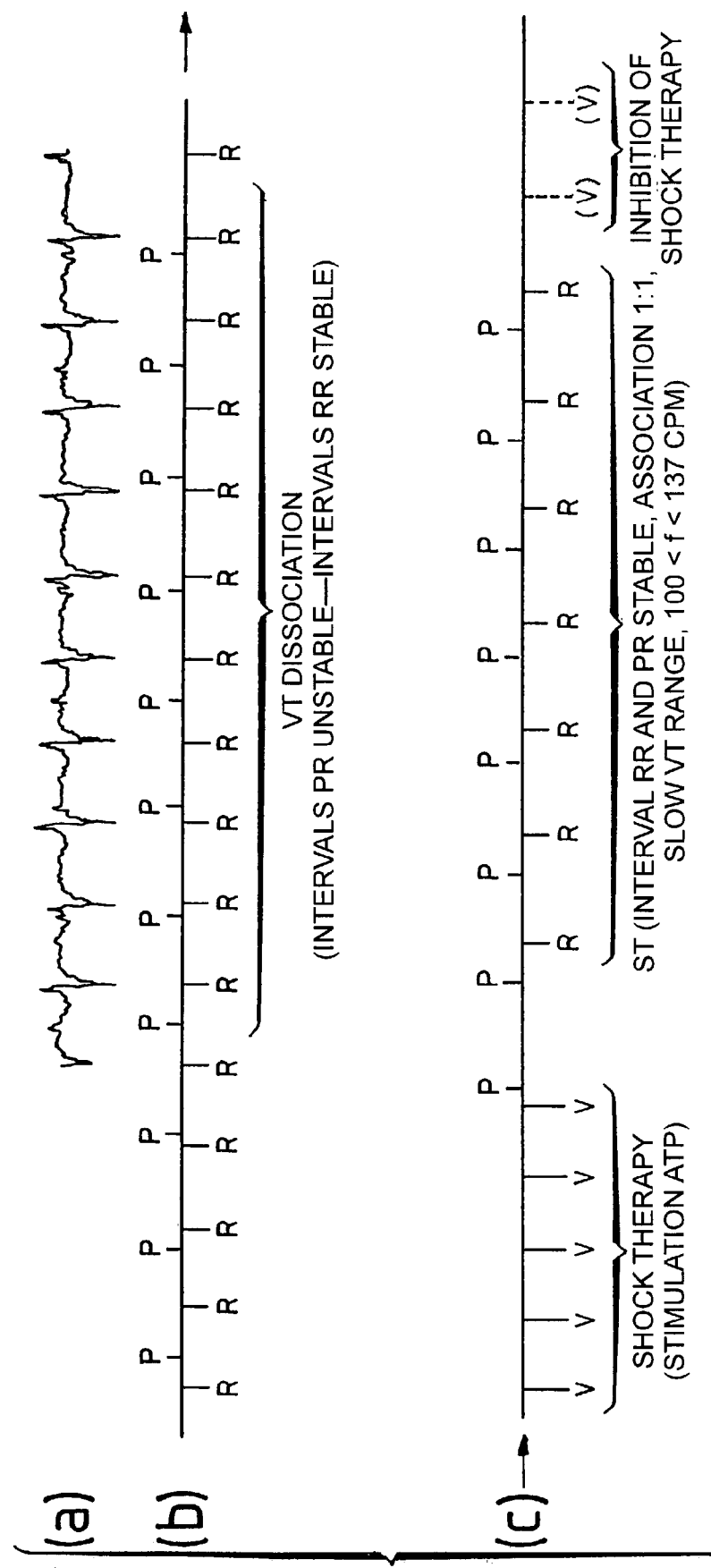
FIG_2

DETECTION OF POST-SHOCK THERAPY SINUSAL TACHYCARDIA IN ACTIVE IMPLANTABLE DEFIBRILLATOR CARDIOVERTOR MEDICAL DEVICES

FIELD OF THE INVENTION

The present invention concerns active implantable medical devices within the meaning of the Jun. 20, 1990 directive 90/385/cee of the Council of the European Communities, and more particularly the family of the devices that deliver to the heart pulses of relatively high energy in order to terminate a tachyarrhythmia (i.e., pulses notably exceeding the energy level typically provided for simple stimulation commonly known as a pacing stimulation pulse).

These high energy pulses also are referred to as "shock (s)", and also can include modes of shock therapy such as a mode of programmed high frequency stimulation or Anti-Tachycardia Pacing ("ATP").

These devices are commonly called "implantable defibrillators" or "cardioversion devices." It should be understood, however, that the present invention is equally applicable to implantable defibrillators/cardiovertors/pacemakers, as well as to implantable defibrillators/pacemakers, and that therapy refers to the application of a defibrillation shock or a cardioversion shock or series of shocks as with an ATP stimulation mode.

BACKGROUND OF THE INVENTION

Tachycardia is a cardiac condition whose symptom is a fast heartbeat rate. There are different types of classifications of tachycardia (also referred to in the literature as "tachyarrhythmia") including: (1) tachyarrhythmias that are pathological in origin, including ventricular fibrillation (VF), ventricular tachycardia (VT) and supra-ventricular tachycardia (SVT), covering atrial tachycardia, atrial flutter and atrial fibrillation (FA); and (2) sinusal tachycardia ("ST") that are physiological in origin.

The diagnosis and the classification of tachycardia are generally performed in a known manner. Suitable examples are described e.g., in EP-A-0 626 182 and its corresponding U.S. Pat. No. 5,462,060 and EP-A-0 838 235 and corresponding U.S. Pat. No. 5,868,793, all commonly assigned herewith to Ela Médical, S. A. Montrouge, France. U.S. Pat. Nos. 5,462,060 and 5,868,793 are incorporated herein by reference in their entirety. The diagnosis and classification described therein are based upon selected criteria such as the ventricular frequency, the stability of the ventricular intervals (RR intervals), an analysis of atrio-ventricular association (such as is revealed by the stability of the PR interval) and the mode of starting of the tachycardia (e.g., a presence of an abrupt acceleration and the cavity of origin of the tachycardia (ventricular or atrial)).

The algorithms used to perform the diagnosis and classification as described in the above mentioned patents are particularly effective to discriminate situations where it is necessary to deliver a ventricular therapy (true VT) from those situations where it is not necessary to do so (ST or SVT, because in their latter cases the tachycardia is of atrial origin and an atrial therapy can be considered).

Clinical implementation of these algorithms and the resultant decision to apply a particular therapy, however, has revealed a difficulty during the time immediately following the application of a therapy. Indeed, after the application of a shock or an ATP stimulation therapy, the algorithm is reiterated to determine whether a therapy must be again applied or, on the contrary, the therapy already applied caused the tachyarrhythmia to disappear, as was the purpose of the delivery of this therapy. The clinical study indeed revealed that certain cases of post-therapy ST were wrongly interpreted by the algorithm as VT, and thus unnecessarily caused the repetition of the therapy.

However, it is desirable to avoid applying a therapy when it is not necessary because, among other things, the unjustified application of a therapy can have noxious (adverse) consequences on the evolution of the heartbeat rate of the patient, the therapy, in particular in the form of a cardioversion or defibrillation shock, is painful for the patient and must thus be limited to cases of necessity, and a repeated therapy will worry the patient and the clinician, who will believe wrongly that the initial therapy was not effective whereas the repetition of the therapy is the result only of an incorrect interpretation of the situation by the algorithm.

OBJECTS AND SUMMARY OF THE INVENTION

It is, therefore, an object of the invention to overcome the above mentioned disadvantage, and to improve the algorithms implemented by the existing devices in order to minimize the risks from false diagnoses of VT corresponding to a post-therapy ST not indicated for delivery of a therapy.

Broadly, the present invention is an improved medical device such as a defibrillator or cardiovertor of the known type as described for example by the EP-A-0 838 235 and U.S. Pat. No. 5,868,793 above mentioned, i.e. including:
  means for sensing the ventricular and atrial activity;
  means for detecting episodes of tachycardia in the sensed activity;
  means for delivering a therapy selected from among a defibrillation shock, a cardioversion shock and/or a ventricular and/or atrial antitachycardia stimulation;
  means for classifying the detected tachycardia according to selected criteria; and
  means for selectively controlling the means for delivering the therapy according to the type of tachycardia determined by the classification means.

According to the invention, this device also includes means for analyzing tachycardia after delivery of a therapy and determining a presence of post-therapy sinusal tachycardia by recognition of a stable ventricular rate, preferably presenting a 1:1 association of ventricular and atrial ventricular rates and a determined heart rate that is in a range corresponding to a slow ventricular tachycardia as determined by the classification means; and means for inhibiting the therapy delivering means in the presence of the determined post-therapy sinusal tachycardia.

In a preferred embodiment, the tachycardia analyzing means determines the presence of a post-therapy sinusal tachycardia based on the heart rate also being lower than a predetermined frequency limit, for example, a heart rate limit that is adjustable in the range between 120 and 160 bpm.

Very advantageously, the device, in accordance with preferred embodiments of the present invention, can be configured to perform one or more of the following functions:

In one preferred embodiment, in the event that the classifying means determines a ventricular fibrillation, an indicator is positioned before delivery of the therapy. The indicator is preferably positioned by establishing a parameter and setting the parameter to a particular value, e.g., logical "1". Then at the following iteration of classification algorithm, in the presence of a determined post-therapy sinusal tachycardia, the therapy delivering means is inhibited if the aforementioned indicator is positioned (e.g., set equal to logical "1"), and to deliver the therapy in the contrary case (e.g., set equal to logical "0").

In yet another embodiment, in the case that the classifying means determines a ventricular tachycardia exists without a 1:1 association, an indicator is positioned to logical "1" before delivery of the therapy and, at the following iteration of classification algorithm, in the presence of a determined post-therapy sinusal tachycardia, the therapy delivering means is inhibited if the aforementioned indicator is positioned, and to deliver the therapy in the contrary case.

As yet another alternative in connection with one or the other of the two preceding embodiments, when the classifying means determines a heart rate that is out of the aforementioned range corresponding to a slow ventricular tachycardia, if the aforementioned indicator were positioned, the algorithm then un-positions the indicator before delivery of the therapy and, at the following iteration, in the presence of a determined post-therapy sinusal tachycardia, inhibits the therapy delivering means if the aforementioned indicator is positioned, and delivers the therapy in the contrary case.

Also, in connection with one or the other of the two above mentioned embodiments, and when the analyzing means of tachycardia compares the heart rate with a predetermined frequency limit, it is advantageously envisaged that in the event of a heart rate higher than the predetermined frequency limit: if the indicator was positioned, to un-position it before delivery of the therapy; and, at the following iteration, in the presence of a determined post-therapy sinusal tachycardia to inhibit delivering the therapy if the aforementioned indicator is positioned, and to deliver the therapy in the contrary case.

In yet another embodiment, it can be envisaged to provide a means for permanently memorizing (i.e., storing in non-volatile memory) the occurrence of a post-therapy sinusal tachycardia determined by the analysis means.

BRIEF DESCRIPTION OF THE DRAWINGS

Further benefits, features and characteristics of the present invention will become apparent to a person of ordinary skill in the art in view of the following detailed description of a preferred embodiment of the invention, made with in reference to the annexed drawings, in which:

FIG. 1 is a flow chart illustrating the function of the discrimination and the classification of the tachyarrhythmias and the selective controlling of a therapy; and FIG. 2 is a chronogram illustrating a sequence of atrial and ventricular events before, during, and after application of a therapy.

DETAILED DESCRIPTION OF THE DRAWINGS

The present invention is directed to an improvement of the algorithm known and described in the aforementioned EP-A-0 626 182, U.S. Pat. No. 5,462,060, and EP-A-0 838 235 and U.S. Pat. No. 5,868,793, which are implemented in the commercial Defender™ and Alto™ defibrillator models of Ela Médical, to operate the detection and the classification of the various tachyarrhythmia according to various known criteria. The person of ordinary skill in the art is specifically directed to refer to these documents for further details regarding the various criteria and the known algorithms and to this end, the disclosures of U.S. Pat. Nos. 5,462,060 and 5,868,793 are incorporated herein by reference in their entirety.

More specifically, however, the classification criteria implemented are:

1) the ventricular frequency;

2) the stability of the ventricular intervals (RR intervals): one defines that there is "stability of the RR intervals" when the peak of autocorrelation, divided by the total of autocorrelation, exceeds a given ratio (the peak of autocorrelation is the maximum number of recent intervals in the ventricle that satisfy a criterion of predetermined stability);

3) the stability of conduction (stability of the PR interval, revealed by the analysis of atrio-ventricular association: one defines that there is stability of conduction when the value of the peak of intercorrelation, divided by the value of the peak of autocorrelation, exceeds a given ratio (the peak of intercorrelation is the maximum number of intervals of conduction coming from the atrium that satisfies a criterion of predetermined stability); in other words, one compares the stability of conduction between the two chambers with those of the intervals in the ventricle;

4) the atrio-ventricular type of association, in 1:1 or n:1, by comparing the peak of intercorrelation to the total of intercorrelation;

5) the starting mode of the tachycardia: i.e., presence of an abrupt acceleration beginning with a dissociation, and the cavity of origin (ventricular or atrial); the criterion of analysis of the acceleration of the ventricular rate and the determination of the origin of this acceleration are described in the EP-A-0 626 182 and U.S. Pat. No. 5,462,060 above mentioned; and 6) the presence or the absence of long cycles: one defines that there is a presence of long cycles if one detects at least one cycle in which the duration of the RR interval is greater than a preset value, for example, expressed in the form (RRmax+StabRR), RRmax being the higher limit of the peak of autocorrelation, and StabRR being a parameterized value defining an interval of safety between this higher limit and the range of detection of the intervals considered as long.

The implementation of this known algorithm makes it possible to discriminate between:

on the one hand, a ventricular tachycardia (VT), which is a tachyarrhythmia that probably has its origin in the ventricle, and that is likely to be stopped by a therapy applied to the ventricle; a therapeutic shock action on the ventricle in this case should thus be authorized;

on the other hand, a supra-ventricular tachycardia (SVT) or a sinusal tachycardia (ST, probably of physiological origin), which is not in any way likely to be stopped by a therapeutic shock action on the ventricle because the origin is in the atrium; any ventricular shock therapy must thus be inhibited (although it is possible to initiate a therapeutic shock action on the atrium in the case of a SVT).

The implementation of this known algorithm allows, as a need, to deliver a therapy when a true VT is detected, by reducing, if not eliminating, the cases of false diagnosis of VT corresponding to a SVT.

Until now, in the devices of prior art, after a therapy is applied, the algorithm is reiterated, just as it is, in order to treat again, if necessary, a repeating tachyarrhythmia. That being said, one could however observe in certain clinical cases false diagnoses, that is certain post-therapy ST being interpreted (wrongly) as VT. These false diagnoses correspond in fact to a situation where one has: stable intervals RR/association/association in 1:1/abrupt acceleration of the ventricle. Concerning the last criterion of abrupt acceleration, insofar as it is examined immediately after a therapy, one does not yet have data on acceleration at the beginning of arrhythmia. Consequently, the algorithm forces by default the criterion of acceleration to be set to "abrupt acceleration of the ventricle". This false diagnosis again starts the therapy application, whereas a therapy was not necessary because, being an ST of physiological origin, the application of a shock to the ventricle will be without effect.

The number of observations of such a case of false diagnosis is increased when a long detection interval is programmed.

It also can be that a slow VT (e.g., a heart rate in the range of 100–150 bpm) can be supported for a certain time by the patient without it being necessary to apply a shock, unlike the cases of a rapid VT (heart rate in the range of 150–200 bpm) and a VF (heart rate higher than 200 bpm); these two last situations require an application of a therapy without significant delay.

The object of this invention is to overcome the above mentioned disadvantages, while proposing to improve the existing devices, so as to minimize the risk of false diagnoses of post-therapy ST (i.e., ST interpreted wrongly as VT), so as also to increase the specificity and the reliability of the analysis of the tachyarrhythmias after application of a therapy.

With reference to FIG. 1, an algorithm implementing the functions according to the invention is shown, that makes it possible to achieve this objective. After initialization of the various parameters (stage 10), an indicator F is positioned to '0' (stage 12).

The following stage (stage 14) implements the tachyarrhythmia detection and classification algorithm as described in the EP-A-0 626 182 and U.S. Pat. No. 5,462,060 (the algorithm referred to as PARAD™) and EP-A-0 838 235 and U.S. Pat. No. 5,868,793 (the algorithm referred to as PARAD+™) above mentioned. At this stage 14, the algorithm is carried out in the same manner as in the prior known devices.

If the disorder is an SVT or an ST (based on the test at stage 16), as known in the prior art, any ventricular therapy is inhibited, and this is done in a systematic manner. The detection and classification algorithm at stage 14 is then reiterated (return to stage 14 from stage 16).

However, in the event of an SVT, an atrial therapy can be considered.

If the disorder is classified as a VF (test at stage 18), as in the prior art a therapy is applied, here still in a systematic manner, but the indicator F is positioned to '1' (stage 20) before the application of the therapy (delivered at stage 22). The detection and classification analysis algorithm 14 is then reiterated after application of the therapy (return to stage 14 from stage 22).

On the assumption that the disorder is none of an SVT, an ST and a VF, the algorithm then examines whether it is a VT (test at stage 24). In the negative case, the therapy is inhibited and the detection and classification algorithm is reiterated (return to stage 14). In the affirmative case, in a manner characteristic of the invention, the device seeks whether it could be a question of a post-therapy ST, therefore likely to be interpreted (wrongly) as a VT. More specifically, if one is in a configuration where one has:

1) 1:1 association (test at stage 26) and
2) a slow VT, for example, a heart rate that is below 137 bpm (test at stage 28), and
3) an absence of therapy applied to the preceding iteration (indicator F positioned to F=0 (test at stage 32), then it is determined as a situation requiring the application of a therapy without significant delay, and that action is carried out at stage 22, followed by a return to stage 14 for another iteration of the detection and classification algorithm.

If, however, at stage 26, the analysis of the rate revealed a dissociation (conduction different from 1:1), then the indicator F is positioned to '1' (stage 20) and the therapy is applied (stage 22).

It is advisable to recall that the VT is diagnosed according to two different ways: (i) RR stable/dissociation, or (ii) RR stable/association 1:1/acceleration of the ventricle (cf. the teaching of the EP-A-0 626 182 and U.S. Pat. No. 5,462,060 mentioned above).

If, at stage 28, the analysis of the rate reveals a fast VT (typically a frequency of the heartbeat rate greater than 137 bpm), then the device applies a therapy (stage 22), but while setting the precondition indicator F to '0' (stage 30), i.e., the indicator F is maintained at '0' if it was, or if it was positioned to F='1', it is then unpositioned or restored to F='0'.

It should be understood that the positioning of indicator F must be as between a first value (e.g., corresponding to a logical high state such as 1) and a second value (e.g., corresponding to a logical low state such as 0) as implemented in a software instruction that sets or unsets a flag having a binary value (although other values could be used).

If at stage 32, the indicator F were positioned to '1', indicating that at the preceding iteration a therapy had been applied following a VF or a VT with dissociation, then the therapy is inhibited and the detection and classification analysis algorithm is reiterated (return to stage 14). One will note that, on the other hand, in the case of a fast VT with association 1:1 (stage 28), the indicator F had been positioned to '0' at stage 30, and the therapy will be delivered and not inhibited because, in this particular case, it must be applied without delay.

With reference to FIG. 2, a series of chronograms illustrate the result of the implementation of the aforementioned algorithm according to a preferred embodiment of the invention.

The line (a) illustrates an ECG waveform, and the lines (b) and (c) (line (c) is a continuation of line (b)) indicates the markers of atrial events (atrial detection P) and ventricular events (ventricular detection R or ventricular stimulation V).

The line (b) shows the appearance of a VT with stable RR intervals, but unstable PR intervals, and an absence of long cycle. This situation will start the application of a therapy, here in the form of ATP stimulation corresponding to a series of ventricular stimuli V at the beginning of the line (c). After application of this therapy, one has illustrated the appearance of an ST, a post-therapy ST, corresponding to a situation with: stable RR and PR intervals, 1:1 association, and a heartbeat rate of 120 bpm (thus located in the slow VT range and below the frequency limit of 137 bpm). In such a situation, the algorithm of the prior art would have caused the application of a therapy, illustrated by the events indicated (v) and illustrated in dash (phantom line) tracing.

The modification made by the algorithm of the present invention allows precisely, in this situation where a therapy is not necessary, to inhibit the delivery of a therapy.

Suitable devices for which the present invention has application include, for example, the Defender™ and Alto™ brand of defibrillators available from Ela Médical, Montrouge France. These devices are capable of receiving by telemetry software instructions to perform the functions described above in implementing the present invention, storing the instructions in memory, and then executing those instructions. The creation of suitable software instructions for controlling an implant having a microprocessor, memory, and cardiac signal acquisition and processing circuits and the control logic to perform the aforementioned functions of the present invention are believed to be within the abilities of a person of ordinary skill in the art.

One skilled in the art will appreciate that the present invention can be practiced by other than the described embodiments, which are presented for purposes of illustration and not of limitation.

We claim:

1. An active implantable medical device including means for sensing ventricular and atrial activity; means for detecting a tachycardia in the sensed activity; means for classifying said detected tachycardia, said classifying means operating in an iterative manner; means for delivering a therapy; and means for selectively controlling the therapy delivering means as a function of the classified tachycardia; wherein the classification means further comprises means for analyzing a post-therapy detected tachycardia and determining whether said post-therapy detected tachycardia corresponds to a post-therapy sinusal tachycardia, and means for inhibiting the therapy delivering means from delivering a therapy in response to the determined post-therapy tachycardia being a post-therapy sinusal tachycardia.

2. The device of claim 1 wherein the classifying means further comprises means for determining an atrial rate and a ventricular rate; means for determining a stability of the ventricular rate; means for determining an association of the atrial and ventricular rates; means for determining whether the ventricular rate is in a predetermined range corresponding to a slow ventricular tachycardia range; and wherein said analyzing means determines a post-therapy sinusal tachycardia as a detected tachycardia having a stable ventricular rate, a 1:1 association of atrial and ventricular rates, and a ventricular rate in said predetermined range.

3. The device of claim 2, further comprising means for comparing the ventricular rate to a predetermined frequency limit, wherein the analyzing means further comprises means for determining that the post-therapy detected tachycardia is a post-therapy sinusal tachycardia in response to the ventricular rate being lower than said predetermined frequency limit.

4. The device of claim 3, further comprising means for adjusting the predetermined frequency limit to a limit between 120 and 160 bpm.

5. The device of claim 2, wherein the classifying means further comprises means for determining a ventricular tachycardia in an absence of 1:1 association, and further comprising means for positioning an indicator to a first value before delivery of the therapy, and further comprising means for inhibiting the therapy delivering means from delivering a therapy in response to a determined post-therapy sinusal tachycardia and said indicator being positioned to said first value.

6. The device of claim 5, wherein the classifying means further comprises means for determining whether the ventricular rate is out of the slow ventricular tachycardia range, and means for positioning said indicator to a second value before delivery of the therapy, and further comprising means for inhibiting the therapy delivering means from delivering a therapy in response to a determined post-therapy sinusal tachycardia and said indicator being positioned to said first value.

7. The device of claim 2, wherein the classifying means further comprises:
means for comparing the ventricular rate to a predetermined frequency limit and determining whether the ventricular rate is higher than the predetermined frequency limit;
means for determining that the detected tachycardia corresponds to a ventricular fibrillation; and
wherein the analyzing means further comprises means for determining that the post-therapy detected tachycardia is a post-therapy sinusal tachycardia in response to the ventricular rate being lower than said predetermined frequency limit;
said device further comprising means for positioning an indicator to a first value before delivery of a therapy, and means for setting the indicator to a second value in response to the ventricular rate being higher than the predetermined frequency limit; and means for inhibiting the therapy delivering means from delivering a therapy in response to a determined post-therapy sinusal tachycardia and said indicator being positioned to said first value.

8. The device of claim 2, wherein the classifying means further comprises;
means for determining a ventricular tachycardia in an absence of a 1:1 association;
means for comparing the ventricular rate to a predetermined frequency limit and determining whether the ventricular rate is higher than the predetermined frequency limit;
wherein the analyzing means further comprises means for determining that the post-therapy detected tachycardia is a post-therapy sinusal tachycardia in response to the ventricular rate being lower than said predetermined frequency limit;
said device further comprising;
means for positioning an indicator to a first value before delivery of the therapy and setting the indicator to a second value in response to the ventricular rate being higher than the predetermined frequency limit; and
means for inhibiting the therapy delivering means from delivering a therapy in response to a determined post-therapy sinusal tachycardia and said indicator being positioned to said first value.

9. The device of claim 1 wherein the classifying means further comprises means for determining that the detected tachycardia corresponds to a ventricular fibrillation and further comprising means for positioning an indicator to a first value before delivery of a therapy, and means for inhibiting the therapy delivering means in response to said indicator being positioned to said first value and a determined post-therapy sinusal tachycardia.

10. The device of the claim 9, wherein the classifying means further comprises means for determining the ventricular rate is out of the slow ventricular tachycardia range, and means for positioning said indicator to a second value before delivery of the therapy, and means for inhibiting the shock therapy delivering means for delivering a therapy in response to a determined post-therapy sinusal tachycardia and said indicator being positioned to said first value.

11. The device of claim 1 further comprising means for memorizing an occurrence of a determined post-therapy sinusal tachycardia.

* * * * *